(12) United States Patent
Disteldorf et al.

(10) Patent No.: US 8,901,343 B2
(45) Date of Patent: Dec. 2, 2014

(54) METHOD FOR PRODUCING CARBOXYLIC ACID ESTERS

(75) Inventors: Walter Disteldorf, Wachenheim (DE); Jarren Peters, Mannheim (DE); Thomas Schäfer, Mannheim (DE); Katrin Friese, Mannheim (DE); Christoph Übler, Lautersheim (DE)

(73) Assignee: BASF SE, Ludwigshafen (DE)

( * ) Notice: Subject to any disclaimer, the term of this patent is extended or adjusted under 35 U.S.C. 154(b) by 274 days.

(21) Appl. No.: 13/140,256

(22) PCT Filed: Dec. 15, 2009

(86) PCT No.: PCT/EP2009/067177
§ 371 (c)(1),
(2), (4) Date: Jun. 16, 2011

(87) PCT Pub. No.: WO2010/076192
PCT Pub. Date: Jul. 8, 2010

(65) Prior Publication Data
US 2011/0251420 A1     Oct. 13, 2011

(30) Foreign Application Priority Data
Dec. 16, 2008   (EP) .................................... 08171796

(51) Int. Cl.
*C07C 67/08*   (2006.01)

(52) U.S. Cl.
CPC ..................................... *C07C 67/08* (2013.01)
USPC ............................................. 560/99; 560/98

(58) Field of Classification Search
USPC ..................................................... 560/98, 99
See application file for complete search history.

(56) References Cited

U.S. PATENT DOCUMENTS

| 5,349,075 | A | * | 9/1994 | van den Berg et al. | ....... 554/170 |
| 5,849,972 | A | | 12/1998 | Vicari et al. | |
| 6,271,410 | B1 | * | 8/2001 | John et al. | ............ 558/443 |
| 6,916,950 | B2 | * | 7/2005 | Gubisch et al. | ............ 560/204 |
| 6,963,014 | B1 | | 11/2005 | Zeller et al. | |
| 7,091,367 | B2 | * | 8/2006 | Moritz et al. | ................ 554/170 |
| 2002/0028963 | A1 | | 3/2002 | Gubisch et al. | |
| 2004/0192957 | A1 | | 9/2004 | Wickens et al. | |

FOREIGN PATENT DOCUMENTS

| EP | 1186593 A2 | 3/2002 |
| WO | WO-92/13818 A1 | 8/1992 |
| WO | WO-95/14647 A1 | 6/1995 |
| WO | WO-00/78702 A1 | 12/2000 |
| WO | WO-0136356 A2 | 5/2001 |

OTHER PUBLICATIONS

U.S. Appl. No. 13/140,239, filed Jun. 16, 2011, Friese et al.
U.S. Appl. No. 13/140,274, filed Jun. 16, 2011, Peters et al.
Cornils, B., et al., "Applied Homogeneous Catalysis with Organometallic Compounds: A Comprehensive Handbook in Two Volumes", Dimerization and Codimerization, Verlag Chemie, (1996), pp. 261-263.
Friedlander, R., et al., "Make plasticizer olefins via n-butene dimerization", Hydrocarbon Processing, vol. 65, (1986), pp. 31-33.
International Search Report for PCT/EP2009/067177, mailing date Jun. 15, 2010.
Translation of International Preliminary Report on Patentability for PCT/EP2009/067177, mailing date Jun. 20, 2011.

* cited by examiner

*Primary Examiner* — Sudhakar Katakam
*Assistant Examiner* — Pancham Bakshi
(74) *Attorney, Agent, or Firm* — Drinker Biddle & Reath LLP

(57) ABSTRACT

The invention relates to a method for producing carboxylic esters by converting a carboxylic acid or a carboxylic acid anhydride or a mixture thereof with an alcohol in a reaction system comprising one or more reactors, wherein reaction water is distilled as alcohol-water-azeotrope with the vapors, the vapors are at least partially condensed, the condensate is separated into an aqueous phase and an organic phase and said organic phase is supplied at least partially back into said reaction system. Components boiling lower than the alcohol are at least partially removed from said returned organic phase such as wherein components boiling lower than alcohol are evaporated and/or distilled off. An enrichment in the reaction system of by-products boiling lower than alcohol is avoided. Alcohol losses can be minimized by discharge currents.

9 Claims, 1 Drawing Sheet

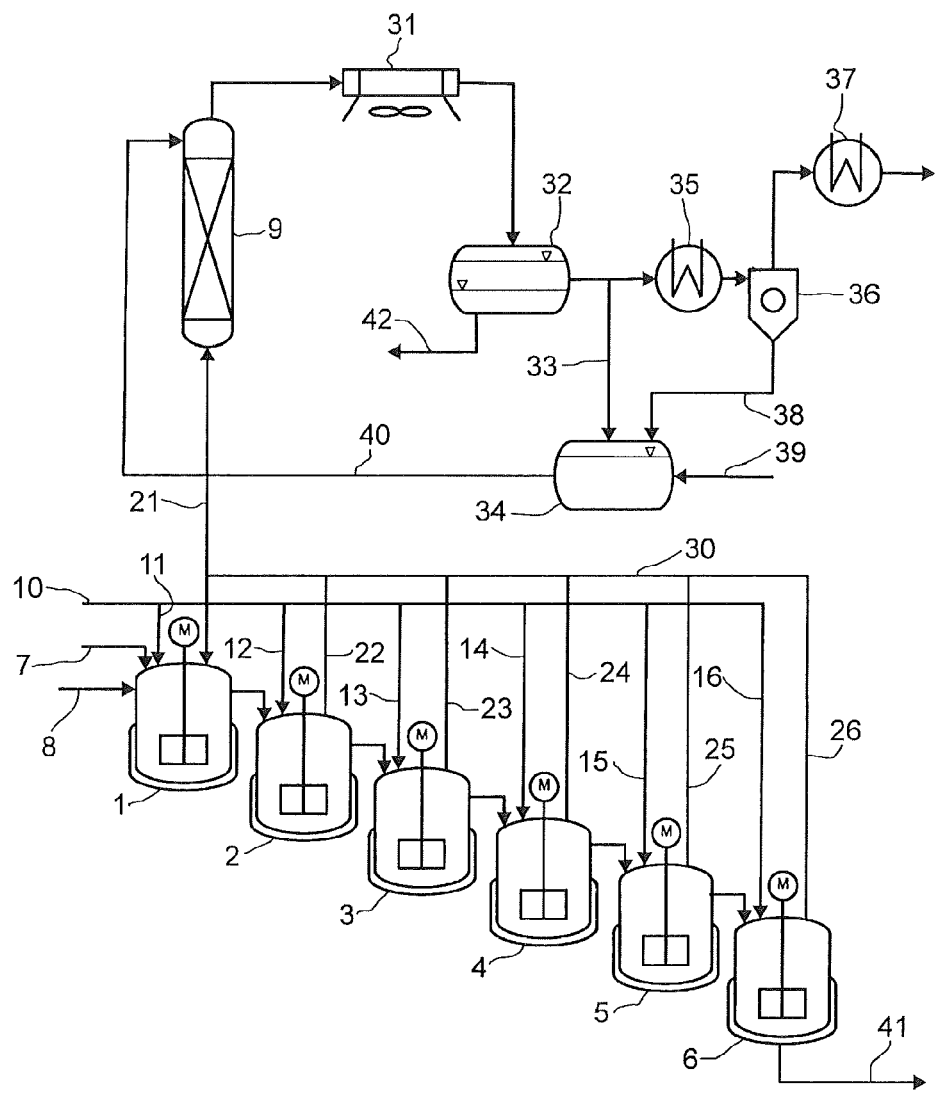

METHOD FOR PRODUCING CARBOXYLIC ACID ESTERS

CROSS-REFERENCE TO RELATED APPLICATIONS

This application is a national stage application (under 35 U.S.C. §371) of PCT/EP2009/067177, filed Dec. 15, 2009, which claims benefit of European application 08171796.9, filed Dec. 16, 2008.

BACKGROUND OF THE INVENTION

The invention relates to a process for preparing carboxylic esters by reacting carboxylic acid or a carboxylic anhydride or a mixture thereof with an alcohol.

Esters of phthalic acid, adipic acid, sebacic acid or maleic acid are widely employed in surface coating resins, as constituents of paints and in particular as plasticizers for plastics.

It is known that carboxylic esters can be prepared by reacting carboxylic acids with alcohols. This reaction can be carried out autocatalytically or catalytically, for example in the presence of Brönsted or Lewis acids as catalysts. Regardless of the type of catalysis, there is always a temperature-dependent equilibrium between the starting materials (carboxylic acid and alcohol) and the products (esters and water).

The reaction of internal carboxylic anhydrides with alcohols proceeds in two steps: the alcoholysis of the anhydride to form the monoester generally proceeds rapidly and to completion. The further conversion of the monoester into the diester with formation of water of reaction is reversible and proceeds slowly. This second step is the rate-determining step of the reaction.

To shift the equilibrium in the direction of the ester (or the full ester in the case of polybasic acids), it is usual to use an entrainer by means of which the water of reaction is removed from the mixture. If one of the starting materials (alcohol or carboxylic acid) has a boiling point lower than that of the ester formed and forms a miscibility gap with water, a starting material can be used as entrainer and be recirculated to the mixture after water has been separated off. In the esterification of higher aliphatic carboxylic acids, aromatic carboxylic acids or dibasic or polybasic carboxylic acids, the alcohol used is generally the entrainer.

EP-A 1 186 593 describes a process for preparing carboxylic esters by reacting dicarboxylic or polycarboxylic acids or anhydrides thereof with alcohols, with the water of reaction being removed by azeotropic distillation with the alcohol. The amount of liquid removed from the reaction by the azeotropic distillation is replaced either completely or partly by the alcohol.

If the alcohol used serves as entrainer, it is usual to condense at least part of the vapor from the reactor, separate the condensate into an aqueous phase and an organic phase comprising essentially the alcohol used for the esterification and recirculate at least part of the organic phase to the reactor. However, various by-products are formed in addition to the desired ester in the esterification reaction. Particularly the by-products having lower boiling points than that of the alcohol are recirculated with the organic phase to the reactor and can, particularly in the case of a continuous process, accumulate in the reaction system.

It has been found that the by-products having boiling points lower than that of the alcohol comprise mainly olefins which have been formed by elimination of water from the alcohol used. Relatively high concentrations of the olefins can damage the esterification catalyst used and/or impair the quality of the ester product produced, in particular lead to undesirable discoloration. To avoid accumulation of the by-products having boiling points lower than that of the alcohol in the reaction system, it is advisable not to recirculate all of the organic phase to the reactor but rather to discharge a substream (purge stream). However, a considerable proportion of the alcohol used is lost to the esterification reaction via the purge stream.

It is therefore an object of the invention to minimize the alcohol losses via the purge stream.

BRIEF SUMMARY OF THE INVENTION

The present invention accordingly provides a process for preparing carboxylic esters by reacting a carboxylic acid or a carboxylic anhydride or a mixture thereof with an alcohol in a reaction system comprising one or more reactors, with water of reaction being distilled off as alcohol-water azeotrope with the vapor, the vapor being at least partly condensed, the condensate being separated into an aqueous phase and an organic phase and at least part of the organic phase being recirculated to the reaction system, wherein components having boiling points lower than that of the alcohol (hereinafter also: "low boilers") are at least partly removed from the organic phase to be recirculated.

BRIEF DESCRIPTION OF THE FIGURE

FIG. 1 shows a plant suitable for carrying out the process of the invention.

DETAILED DESCRIPTION OF THE INVENTION

For the purposes of the present invention, a "reaction system" is a reactor or an assembly of a plurality of reactors. In the case of a plurality of reactors, these are preferably connected in series. "Recirculation to the reaction system" means that an organic phase is introduced into at least one reactor which may be chosen freely of the reaction system. The process of the invention can be carried out batchwise or continuously, but is preferably carried out continuously. The low boilers comprise or consist essentially of olefins (generally olefin isomer mixtures) which are derived from the alcohol used by elimination of water.

The reactors can be any reactors which are suitable for carrying out chemical reactions in the liquid phase.

Suitable reactors are reactors which are not backmixed, e.g. tube reactors or residence vessels provided with internals, but preferably backmixed reactors such as stirred vessels, loop reactors, jet loop reactors or jet nozzle reactors. However, combinations of successive backmixed reactors and reactors which are not backmixed can also be used.

If appropriate, a plurality of reactors can also be combined in a multistage apparatus. Such reactors are, for example, loop reactors with built-in sieve trays, cascaded vessels, tube reactors with intermediate feed points or stirred columns.

In a further process variant, the reaction can be carried out in a reactive distillation column. Such columns have a long residence time of the reaction solution in the respective stage. Thus, for example, columns which have a high liquid hold-up, e.g. highly banked-up trays of a tray column, can advantageously be used.

Preference is given to using stirred tank reactors. The stirred tank reactors are usually made of metallic materials, with stainless steel being preferred. The reaction mixture is preferably intensively mixed by means of a stirrer or a circulation pump.

Even though the process of the invention can be carried out using only one reactor, it is nevertheless advantageous to connect a plurality of reactors, e.g. stirred vessels, to one another in the form of a reactor cascade in order to obtain a substantially complete reaction. The reaction mixture passes through the individual reactors in succession, with the discharge from the first reactor being fed to the second reactor, the discharge from the second reactor being fed to the third reactor, etc. The reactor cascade can comprise, for example, from 2 to 10 stages, with from 4 to 6 stages being preferred.

During the reaction, an alcohol/water mixture is distilled off as azeotrope from the reaction mixture. In addition, further alcohol is fed into the reactor or the individual reactors of the reaction system during the reaction. It is advantageous to feed alcohol into the respective reactor at a predetermined flow rate. The flow rate can be adapted as a function of the periodically measured acid number of the reaction mixture in the respective reactor.

The condensation or partial condensation of the vapor can be effected using all suitable condensers. These can be cooled by means of any cooling media. Condensers having air cooling and/or water cooling are preferred, and air cooling is particularly preferred.

The condensate obtained is subjected to a phase separation into an aqueous phase and an organic phase. For this purpose, the condensate is usually introduced into a phase separator (decanter) where it separates by mechanical settling into two phases which can be taken off separately. The aqueous phase is separated off and can, if appropriate after work-up, be discarded or used as stripping water in the after-treatment of the ester.

The vapor from the individual stirred vessels of a cascade can be combined and subject together to the removal of low boilers according to the invention. It has been found that even only one condenser and one apparatus for separating off low boilers can be sufficient to achieve effective treatment of the vapors coming from a plurality of vessels of a cascade.

If appropriate, a plurality of vessels of the cascade can be combined to form one subunit, with the subunits then each being coupled to a condenser and an apparatus for separating off low boilers. It is also possible to couple each vessel of the cascade with a condenser.

The organic phase treated according to the invention and to be recirculated can be passed into any reactor of a cascade or distributed over a plurality of reactors of the cascade. However, the organic phase treated according to the invention and to be recirculated is preferably not introduced into the last reactor of the cascade. The organic phase treated according to the invention and to be recirculated is preferably introduced exclusively or predominantly into the first reactor of the cascade.

There are various possibilities for the recirculation of the organic phase into the reaction system. One possibility is to pump the organic phase, if appropriate after heating, into the liquid reaction mixture.

However, to thermally optimize the process, the organic phase is preferably recirculated into the reaction system via a column (known as recycle alcohol column) in which the organic phase recirculated is conveyed in countercurrent to at least part of the vapor. The organic phase is advantageously introduced into the recycle alcohol column at the top or in the upper region. The descending condensate of the recycle alcohol column goes back into the reaction system, when a reactor cascade is used preferably into the first reactor. The recirculation of the organic phase via the recycle alcohol column has the advantage that the recirculated organic phase is preheated and freed of traces of water which have remained in the organic phase after the phase separation or are, in accordance with their thermodynamic solubility, dissolved in the organic phase. The recycle alcohol column can be, for example, a tray column, a column having ordered packing or a column having random packing elements. A small number of theoretical plates is generally sufficient. A column having, for example, from 2 to 10 theoretical plates is suitable.

When a reactor cascade is used, the vapor preferably leaves at least the first reactor via the recycle alcohol column. One or more or all further reactors can likewise have a vapor offtake to the recycle alcohol column.

According to the invention, components having boiling points lower than that of the alcohol are at least partly removed from the organic phase to be recirculated. Here, the boiling point differences between olefin/alcohol and olefin-water azeotrope/alcohol-water azeotrope are exploited. The order of boiling points is illustrated below for the example of 1-nonene/1-nonanol and their azeotropes with water:

|  | Boiling point [° C.] |
| --- | --- |
| 1-Nonene-water minimum heteroazeotrope | 94.327 |
| 1-Nonanole-water minimum heteroazeotrope | 99.719 |
| 1-Nonene | 146.903 |
| 1-Nonanol | 213.396 |

In one embodiment of the process, the vapor comprising the alcohol-water azeotrope is condensed incompletely, resulting in components having boiling points lower than that of the alcohol accumulating in the uncondensed vapor and being able to be discharged with the uncondensed vapor. The condensate is separated into an aqueous phase and an organic phase comprising essentially alcohol and the organic phase is at least partly recirculated to the reaction system.

Incomplete condensation of the vapor can be achieved by appropriate selection of the temperature in the condenser, e.g. by choice of the temperature and/or flow of the cooling medium. To effect incomplete condensation of the vapor, the latter can also be introduced e.g. as bottom or side feed stream, into a column. The uncondensed vapor can be condensed in an after-condenser and, for example, passed to thermal utilization.

In this embodiment, the separation of alcohol and low boilers occurs in the presence of water; the separation is based on the different boiling points of the alcohol-water azeotrope and the olefin-boiler azeotrope. As is shown in the table above, the boiling point difference between the azeotropes is not pronounced, so that only incomplete separation is possible at a small number of theoretical plates. In addition, formation of complex mixtures which comprise not only the alcohol-water azeotrope and the olefin-water azeotrope but also alcohol, olefin, etc., can occur. Since the boiling point of the alcohol-water azeotrope is generally lower than the boiling point of the olefin, only incomplete removal of the low boilers is achieved in this embodiment. The uncondensed vapor therefore still comprises a large proportion of alcohol which is lost to the esterification reaction.

In another, preferred embodiment of the process, the vapor comprising alcohol-water azeotrope is therefore at least partly condensed, in particular essentially completely condensed, and the condensate is separated into an aqueous phase and an organic phase. At least part of the organic phase is treated by evaporating and/or distilling off components having boiling points lower than that of the alcohol and recirculating at least part of the organic phase which has been treated in this way to the reaction system. The low boilers which have been evaporated or distilled off can be condensed in an after-condenser and, for example, passed to thermal utilization.

In this embodiment, the separation of alcohol and low boilers occurs in the substantial absence of water. Since the alcohol and the olefin generally have a large boiling point difference (cf. the table above), simple distillation or distillation using a small number of theoretical plates is usually sufficient to achieve substantial removal of the low boilers.

To avoid accumulation of low boilers in the reaction system, it has been found to be sufficient to treat only part of the organic phase before it is recirculated to the reaction system. In a useful embodiment, part of the organic phase is therefore recirculated unchanged to the reaction system and another part of the organic phase is treated by evaporating and/or distilling off components having boiling points lower than that of the alcohol and recirculating at least part of the organic phase which has been treated in this way to the reaction system. Preference is given to treating at least 20% of the total organic phase, in particular from 25 to 60%, e.g. from 30 to 40% of the total organic phase, obtained in the phase separation.

The evaporation or distillation of the components having boiling points lower than that of the alcohol can be carried out in any apparatuses suitable for this purpose, e.g. a distillation column or an evaporator of any construction type, e.g. stirred evaporator, oblique-tube evaporator, vertical-tube evaporator with natural or forced convection, climbing film evaporator, falling film evaporator, horizontal-tube evaporator, Robert evaporator, Herbert evaporator, immersed-tube evaporator, spiral evaporator, plate evaporator, Sambay evaporator or similar apparatuses. The bottom product from the column or the evaporator is at least partly recirculated to the reaction system.

Suitable columns are, for example, tray columns or columns comprising ordered packing or random packing elements. It is advantageous to return part of the overhead condensate, if appropriate after phase separation and removal of the entrained aqueous phase, as runback to the column. The other part of the overhead condensate is discharged from the process.

In many cases, depressurization vaporization is suitable. For this purpose, at least part of the organic phase is depressurized into a depressurization vessel, resulting in at least part of the components having boiling points lower than that of the alcohol vaporizing, and the unvaporized liquid phase is at least partly recirculated to the reaction system. The pressure difference in the depressurization is, for example, at least 500 mbar to a final pressure of less than 500 mbar, preferably less than 200 mbar. If appropriate, the organic phase can be heated by indirect heat exchange before depressurization. Suitable heat exchangers are, for example, shell-and-tube heat exchangers, double-tube heat exchangers, plate heat exchangers, spiral heat exchangers, finned-tube heat exchangers and the like. The temperature of the organic phase before the depressurization is selected according to the boiling points of the alcohol or the olefin and according to the pressure difference in the depressurization.

The temperature is preferably sufficient for the low boilers to be essentially completely vaporized in the depressurization.

The process of the invention can in principle be applied to all esterifications in which the water of reaction is separated off by distillation as azeotrope with an alcohol.

In the process of the invention, carboxylic acids or carboxylic anhydrides are used as acid component. In the case of polybasic carboxylic acids, it is also possible to use partial anhydrides. It is likewise possible to use mixtures of carboxylic acids and anhydrides.

These acids can be aliphatic, including carbocyclic, heterocyclic, saturated or unsaturated, or else aromatic, including heteroaromatic.

Suitable carboxylic acids include aliphatic monocarboxylic acids having at least 5 carbon atoms, in particular from 5 to 20 carbon atoms, e.g. n-pentanoic acid, 2-methylbutyric acid, 3-methylbutyric acid, 2-methylpentanoic acid, 2-ethylbutyric acid, n-heptanoic acid, 2-methylhexanoic acid, isoheptanoic acids, cyclohexanecarboxylic acid, n-octanoic acid, 2-ethylhexanoic acid, isooctanoic acids, n-nonanoic acid, 2-methyloctanoic acid, isononanoic acids, n-decanoic acid, isodecanoic acids, 2-methylundecanoic acid, isoundecanoic acid, tricyclodecanecarboxylic acid and isotridecanoic acid.

Further suitable carboxylic acid components are aliphatic $C_4$-$C_{10}$-dicarboxylic acids or anhydrides thereof, e.g. maleic acid, fumaric acid, maleic anhydride, succinic acid, succinic anhydride, adipic acid, subacic acid, trimethyladipic acid, azelaic acid, decanedioic acid, dodecanedioic acid, brassylic acid. Examples of carbocyclic compounds are: 1,2-cyclohexanedicarboxylic acid (hexahydrophthalic acid), 1,2-cyclohexanedicarboxylic anhydride (hexahydrophthalic anhydride), cyclohexane-1,4-dicarboxylic acid, cyclohex-4-ene-1,2-dicarboxylic acid, cyclohexene-1,2-dicarboxylic anhydride, 4-methylcyclohexane-1,2-dicarboxylic acid, 4-methylcyclohexane-1,2-dicarboxylic anhydride, 4-methylcyclohex-4-ene-1,2-dicarboxylic acid, 4-methylcyclohex-4-ene-1,2-dicarboxylic anhydride.

Examples of suitable aromatic dicarboxylic acids or anhydrides thereof are: phthalic acid, phthalic anhydride, isophthalic acid, terephthalic acid or naphthalenedicarboxylic acids and anhydrides thereof.

Examples of suitable aromatic tricarboxylic acids (or anhydrides) are trimellitic acid, trimellitic anhydride or trimesic acid; an example of a suitable aromatic tetracarboxylic acid or anhydride thereof is pyromellitic acid and pyromellitic anhydride.

Particular preference is given to using phthalic anhydride as carboxylic acid component in the process of the invention.

Preference is given to using branched or linear aliphatic alcohols having from 4 to 13 carbon atoms, in particular from 9 to 13 carbon atoms, in the process of the invention. The alcohols are monohydric and can be secondary or primary.

The alcohols used can originate from various sources. Suitable starting materials are, for example, fatty alcohols, alcohols from the Alfol process or alcohols or alcohol mixtures obtained by hydrogenation of saturated or unsaturated aldehydes, in particular ones whose synthesis includes a hydroformylation step.

Alcohols which are used in the process of the invention, are, for example, n-butanol, isobutanol, n-octan-1-ol, n-octan-2-ol, 2-ethylhexanol, nonanols, decyl alcohols or tridecanols prepared by hydroformylation or aldol condensation and subsequent hydrogenation. The alcohols can be used as pure compounds, as a mixture of isomeric compounds or as a mixture of compounds having different numbers of carbon atoms. A preferred example of such an alcohol mixture is a $C_9$/$C_{11}$-alcohol mixture.

Preferred feed alcohols are mixtures of isomeric octanols, nonanols or tridecanols, with the latter being able to be obtained from the corresponding butene oligomers, in particular oligomers of linear butenes, by hydroformylation and subsequent hydrogenation. The preparation of the butene oligomers can in principle be carried out by three methods. Acid-catalyzed oligomerization, in which, for example, zeolites or phosphoric acid on supports are used industrially, gives the most branched oligomers. For example, the use of linear butenes gives a $C_8$ fraction comprising essentially dimethylhexenes (WO 92/13818). A process which is likewise practiced worldwide is oligomerization using soluble Ni complexes, known as the DIMERSOL process (B. Cornils, W. A. Herrmann, Applied Homogenous Catalysis with Organometallic Compounds, pages 261-263, Verlag Chemie 1996). In addition, oligomerization is carried out over fixed-bed nickel catalysts, for example the OCTOL process (Hydrocarbon Process., Int. Ed. (1986) 65 (2. Sect. 1), pages 31-33) or the process as described in WO 95/14647 or WO 01/36356.

Very particularly preferred starting materials for the esterification according to the invention are mixtures of isomeric nonanols or mixtures of isomeric tridecanols prepared by oligomerization of linear butenes to $C_8$-olefins and $C_{12}$-olefins by the octol process or as described in WO 95/14647, with subsequent hydroformylation and hydrogenation.

Further suitable alkyls are alkylene glycol monoethers, in particular ethylene glycol monoethers such as ethylene glycol monomethyl ether, ethylene glycol monoethyl ether and ethylene glycol monobutyl ether; and polyalkylene glycol monoethers, in particular polyethylene glycol monoethers such as polyethylene glycol monomethyl ether.

Particularly preferred alcohols are 2-ethylhexanol, 2-propylheptanol, isononanol isomer mixtures, decanol isomer mixtures and $C_9/C_{11}$-alcohol mixtures.

The esterification according to the invention can be autocatalyzed or can be carried out in the presence of an esterification catalyst. The esterification catalyst is appropriately selected from among Lewis acids such as alkoxides, carboxylates and chelate compounds of titanium, zirconium, tin, aluminum and zinc; boron trifluoride, boron trifluoride etherates; mineral acids such as sulfuric acid, phosphoric acid; sulfonic acids such as methanesulfonic acid and toluenesulfonic acid, and ionic liquids.

The esterification catalyst is appropriately selected from among alkoxides, carboxylates and chelate compounds of titanium, zirconium, tin, aluminum and zinc. Suitable catalysts are tetraalkyl titanates such as tetramethyl titanate, tetraethyl titanate, tetra-n-propyl titanate, tetraisopropyl titanate, tetra-n-butyl titanate, tetraisobutyl titanate, tetra-sec-butyl titanate, tetraoctyl titanate, tetra(2-ethylhexyl) titanate; dialkyl titanates ($(RO)_2TiO_2$, where R is, for example, isopropyl, n-butyl, isobutyl), e.g. isopropyl n-butyl titanate; titanium acetylacetonate chelates such as diisopropoxy bis(acetylacetonate)titanate, diisopropoxy bis(ethylacetylacetonate)titanate, di-n-butyl bis(acetylacetonate)titanate, di-n-butyl bis(ethylacetoacetato) titanate, triisopropoxy bis(acetylacetonate)titanate; zirconium tetraalkoxides such as zirconium tetraethoxide, zirconium tetrabutoxide, zirconium tetrabutyrate, zirconium tetrapropoxide, zirconium carboxylates such as zirconium diacetate; zirconium acetylacetonate chelates such as zirconium tetra(acetylacetonate), tributoxyzirconium acetylacetonate, dibutoxyzirconium bisacetylacetonate; aluminum tris-alkoxides such as aluminum triisopropoxide, aluminum trisbutoxid; aluminum acetylacetonate chelates such as aluminum tris(acetylacetonate) and aluminum tris(ethylacetylacetonate). In particular, isopropyl n-butyl titanate, tetra(isopropyl) orthotitanate or tetra(butyl) orthotitanate are used.

Suitable ionic liquids are, for example, 1-(4-sulfobutyl)-3-methylimidazolium triflate and 1-ethyl-3-methylimidazolium hydrogensulfate.

The catalyst concentration depends on the type of the catalyst. In the case of the titanium compounds which are preferably used, this is from 0.005 to 1.0% by weight based on the reaction mixture, in particular from 0.01 to 0.3% by weight.

When the process is carried out batchwise, the starting materials and the catalyst can be introduced into the reactor either simultaneously or in succession. The catalyst can be introduced in pure form or as a solution, preferably as a solution in one of the starting materials, at the beginning or only after the reaction temperature has been reached. Carboxylic anhydrides frequently react autocatalytically, i.e. in the absence of catalysts, with alcohols to form the corresponding ester carboxylic acids (half esters), for example phthalic anhydride to form the monoester of phthalic acid. A catalyst is therefore frequently necessary only after the first reaction step.

In the case of a continuous process, streams of the starting materials and of the catalyst are fed into the reactor or, when a reactor cascade is used, into the first reactor of the cascade. The residence time in the reactor or the individual reactors is determined by the volume of the reactors and the flow of the starting materials.

The alcohol to be reacted, which serves as entrainer, can be used in a stoichiometric excess, preferably from 30 to 200%, particularly preferably from 50 to 100%, of the stoichiometrically required amount.

The reaction temperatures are in the range from 160° C. and 270° C. The optimal temperatures depend on the starting materials, the progress of the reaction and the catalyst concentration. They can easily be determined experimentally for each individual case. Higher temperatures increase the reaction rates and promote secondary reactions such as olefin formation or the formation of colored by-products. To remove the water of reaction, it is necessary for the alcohol to be able to be distilled off from the reaction mixture. The desired temperature or the desired temperature range can be set via the pressure in the reactor. In the case of low-boiling alcohols, the reaction can therefore be carried out under superatmospheric pressure and in the case of relatively high-boiling alcohols under reduced pressure. For example, the reaction of phthalic anhydride with a mixture of isomeric nonanols in the temperature range from 170° C. to 250° C. is carried out in the pressure range from 200 mbar to 3 bar.

All reactors of a cascade can be operated at the same temperature. However, preference is generally given to steadily increasing the temperature from the first to last reactor of a cascade, with a reactor being operated at the same temperature or a higher temperature than the reactor located upstream (based on the flow direction of the reaction mixture). All reactors can advantageously be operated at essentially the same pressure, in particular about ambient pressure.

After the reaction is complete, the reaction mixture, which comprises essentially the desired ester and excess alcohol, further comprises not only the catalyst and/or its reaction products but also small amounts of ester carboxylic acid(s) and/or unreacted carboxylic acid.

To work up these crude ester mixtures, the excess alcohol is removed, the acidic compounds are neutralized, the catalyst is destroyed and the solid by-products formed are separated off. Here, the major part of the unreacted alcohol is distilled off at atmospheric pressure or under reduced pressure. The last traces of the alcohol can be removed, for example, by steam distillation, in particular in the temperature range from 120 to 225° C. under reduced pressure. The removal of the alcohol can be carried out as first or last work-up step.

The neutralization of the acidic substances such as carboxylic acids, ester carboxylic acids or if appropriate the acidic catalysts is effected by addition of bases, e.g. alkali metal and/or alkaline earth metal carbonates, hydrogencarbonates or hydroxides. The neutralizing agent can be used in solid form or preferably as a solution, in particular as an aqueous solution. Here, sodium hydroxide solution having a concentration of from 1 to 30% by weight, preferably from 20 to 30% by weight, is frequently used. The neutralizing agent is used in an amount corresponding to from one to four times, in particular from one to two times, the stoichiometrically required amount determined by titration.

The esters of polybasic carboxylic acids, for example phthalic acid, adipic acid, sebacic acid, maleic acid, and alcohols which have been prepared in this way are used further in surface coating resins, as constituents of paints and in particular as plasticizers for plastics. Suitable plasticizers for PVC are dioctyl phthalate, diisononyl phthalate, diisodecyl phthalate and dipropylheptyl phthalate.

The invention is illustrated by the accompanying drawing and the following examples.

FIG. 1 shows a plant suitable for carrying out the process of the invention. The plant comprises a cascade of six stirred vessels 1, 2, 3, 4, 5 and 6, with the outflow from the first vessel being fed to the second vessel, the outflow from the second vessel being fed to the third vessel, etc. Alcohol is fed via the alcohol manifold 10 and feed lines 11, 12, 13, 14, 15 and 16 into the stirred vessels 1, 2, 3, 4, 5 and 6. Esterification catalyst is added to the first vessel 1 via line 8. An acid component, for example phthalic anhydride (PAn), is fed via line 7 into the first vessel 1.

The vapor space of the first vessel 1 communicates via line 21 with the recycle alcohol column 9, with the vapors ascending from the first vessel 1 being taken off via line 21 and runback from the recycle alcohol column 9 likewise being conveyed via line 21 back into the first vessel 1. The vapor offtakes 22, 23, 24, 25, 26 from the second to sixth vessels 2, 3, 4, 5, 6 are combined via the vapor collection line 30 and likewise lead via line 21 to the recycle alcohol column 9.

The combined vapors are fed to a condenser 31, e.g. and air-cooled condenser. The mixed-phase stream leaving the condenser 31 is separated in the phase separator 32. The lower, aqueous phase is taken off via line 42. The upper, organic phase is partly fed via line 33 to the recycle alcohol collection vessel 34. Another part of the organic phase from the phase separator 32 is heated in the optional heat exchanger 35 and depressurized into the depressurization vessel 36. As a result of the depressurization, the organic phase separates into a vapor fraction is enriched in the low boilers and an alcohol-enriched liquid fraction. The vapor fraction can be condensed in the after-condenser 37 and passed to a use. The liquid fraction is conveyed via line 38 to the recycle alcohol collection vessel 34. Alcohol which is separated off from the crude ester mixture during the work-up can be fed via line 39 to the recycle alcohol collection vessel 34 and thus likewise be passed to reuse. The alcohol from the recycle alcohol collection vessel 34 is fed via line 40 into the top or the upper region of the recycle alcohol column 9 where it is conveyed in countercurrent to the ascending vapors and it goes via line 21 back into the first vessel 1.

EXAMPLES

Example 1

Preparation of Diisononyl Phthalate

The continuous preparation of 2000 g/h of diisononyl phthalate (DINP) was carried out using a cascade of 4 stirred vessels. Isononanol was fed into each reaction vessel, a total of 1380 g/h of isononanol. 0.05% by weight of isopropyl-n-butyltitanate, based on the reaction mixture, is metered into the first reaction vessel. In addition, 708 g/h of phthalic anhydride (PAn) were introduced into the first reaction vessel. By means of a recycle alcohol column on the first reactor, about 1330 g/h of isononanol mixture recycle stream were fed as runback to the recycle alcohol column.

The vapors from the first reactor were taken off via the recycle alcohol column whose runback was fed back into the first reactor. The offtake of vapor from the second to fourth reactor likewise occurred via the recycle alcohol column.

The vapors from the esterification were condensed in a water condenser and the condensate was cooled to a temperature of 70° C. The organic and aqueous phases were separated at atmospheric pressure in a phase separator. The water was discharged from the system; part of the organic phase (300 g/h; about 95% isononanol, 4% isononene) was fed recirculated via an alcohol collection vessel directly into the esterification step.

149 g/h of the organic phase were heated to 100° C. by means of a preheater and fed into a single-stage flash evaporator operated at 100 mbar. The vapor phase from this flash evaporator was condensed in an after-condenser (about 48% of water, 23% of isononanol, 29% of isononene) and discharged from the process (7.3 g/h, of which 1.7 g/h was isononanol). The liquid phase depleted in low boilers (isononene) from the flash evaporator (141.7 g/h, 97% of isononanol) was introduced into the alcohol collection vessel and from there recirculated to the esterification.

An alcohol loss of 0.85 g per kg of DINP, (corresponding to 0.12 mol % of yield) therefore occurred.

Comparative Example 1

The continuous preparation of DINP was carried out in a manner analogous to Example 1, but the organic phase taken off in the phase separator was recirculated without aftertreatment to the esterification. To prevent accumulation of isononene in the isononanol recycle stream, part of the organic phase had to be continuously discharged from the process.

Isononene contents of more than 5% by weight in the isononanol recycle stream can lead to appreciable impairment of the product quality. To limit the isononene content in the isononanol recycle stream to not more than 5% by weight, 160 g/h of organic phase had to be discharged in the preparation of 2000 g/h of DINP, corresponding to an alcohol loss of 76 g per kg of DINP (9.93 mol % of yield).

Example 2

Preparation of Dipropylheptyl Phthalate (Using a Single-Stage Flash Evaporator for Discharge of Low Boilers)

The continuous production of 1280 g/h of dipropylheptyl phthalate from PAn and 2-propylheptanol (2-PH) in the presence of isopropyl n-butyltitanate as catalyst was carried out using a cascade of 4 stirred vessels. The vapors from the esterification were condensed and the condensate was cooled to a temperature of 85° C. Organic and aqueous phases were separated at atmospheric pressure in a phase separator. The water was discharged from the system.

Part of the organic phase was heated to 120° C. by means of a preheater and depressurized into a depressurization vessel maintained at 80 mbar. The vapor phase formed in the depressurization was condensed (0.1% of water, 27.8% of 2-PH, 72.1% of decene) and discharged from the process (7.3 g/h, of which 2 g/h was 2-PH). The liquid phase depleted in low boilers from the depressurization was introduced into an alcohol collection vessel and from there recirculated to the esterification.

An alcohol loss of 1.6 g per kg of dipropylheptyl phthalate (corresponding to 0.23 mol % of yield) therefore occurred.

Example 3

Preparation of Dipropylheptyl Phthalate (Using a Column for the Discharge of Low Boilers)

The preparation of 1280 g/h of dipropylheptyl phthalate from PAn and 2-propylheptanol was carried out in a manner analogous to Example 2. However, part of the organic phase was heated to 130° C. by means of a preheater and fed into a column operated at 80 mbar. The vapor phase from this column was condensed (12.7 g/h) and separated into an organic phase and an aqueous phase in a phase separator. The aqueous phase (2.1 g/h, 99.9% by weight of water, 0.1% by weight of decene) was discarded. About half of the organic phase was fed as runback to the column, while the other part was discharged from the process (5.2 g/h, pure decene).

The bottom product from the column was introduced into the alcohol collection vessel and from there recirculated to the esterification (127.1 g/h, 86% of 2-PH, 14% of decene). In this way, the alcohol loss via the discharge of low boilers was avoided completely.

The invention claimed is:

1. A process for preparing carboxylic esters by reacting a carboxylic acid or a carboxylic anhydride or a mixture thereof with an alcohol in the presence of an esterification catalyst selected from among alkoxides, carboxylates and chelate compounds of titanium, zirconium, tin, aluminum and zinc, in a reaction system comprising one or more reactors, with
   a) water of reaction being distilled off as alcohol-water azeotrope with the vapor,
   b) the vapor being at least partly condensed,
   c) the condensate being separated into an aqueous phase and an organic phase,
   d) part of the organic phase being recirculated unchanged to the reaction system and 25 to 60% of the total organic phase being treated by evaporating and/or distilling off components having boiling points lower than that of the alcohol, wherein said evaporating and/or distilling off components having boiling points lower than that of the alcohol comprises depressurizing into a depressurization vessel, resulting in at least part of the components having boiling points lower than that of the alcohol evaporating, and
   e) the unvaporized liquid phase being at least partly recirculated to the reaction system,
   where the components having boiling points lower than that of the alcohol comprise olefins which are derived by elimination of water from the alcohol used.

2. The process according to claim 1, wherein the vapor is incompletely condensed, components having boiling points lower than that of the alcohol are discharged with the uncondensed vapor, the condensate is separated into an aqueous phase and an organic phase and the organic phase is at least partly recirculated to the reaction system.

3. The process according to claim 1, wherein the organic phase is heated by indirect heat exchange before the depressurization.

4. The process according to claim 1, wherein the organic phase is recirculated to the reaction system via a column in which the recirculated organic phase is conveyed in countercurrent to at least part of the vapor.

5. The process according to claim 1, wherein the reaction system comprises a cascade of a plurality of reactors.

6. The process according to claim 5, wherein the organic phase is recirculated exclusively or predominantly into the first reactor of the cascade.

7. The process according to claim 1, wherein the carboxylic acid is selected from among aliphatic monocarboxylic acids having at least 5 carbon atoms, aliphatic $C_4$-$C_{10}$-dicarboxylic acids, aromatic monocarboxylic acids, aromatic dicarboxylic acids, aromatic tricarboxylic acids, aromatic tetracarboxylic acids and anhydrides thereof.

8. The process according to claim 1, wherein the alcohol is selected from among C4-C13-alcohols, alkylene glycol monoethers, polyalkylene glycol monoethers and mixtures thereof.

9. The process according to claim 1, wherein in step d) 30% to 40% of the total organic phase is treated by evaporating and/or distilling off components having boiling points lower than that of the alcohol.

* * * * *